United States Patent  
Azizian

(10) Patent No.: US 11,997,473 B2
(45) Date of Patent: May 28, 2024

(54) SYSTEM AND METHOD FOR AUDIO SIGNAL PLACEMENT AND PROJECTION

(71) Applicant: INTUITIVE SURGICAL OPERATIONS, INC., Sunnyvale, CA (US)

(72) Inventor: Mahdi Azizian, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 188 days.

(21) Appl. No.: 17/636,496

(22) PCT Filed: Aug. 7, 2020

(86) PCT No.: PCT/US2020/045380
§ 371 (c)(1),
(2) Date: Feb. 18, 2022

(87) PCT Pub. No.: WO2021/034516
PCT Pub. Date: Feb. 25, 2021

(65) Prior Publication Data
US 2022/0286801 A1 Sep. 8, 2022

Related U.S. Application Data

(60) Provisional application No. 62/889,086, filed on Aug. 20, 2019.

(51) Int. Cl.
H04S 7/00 (2006.01)
A61B 34/35 (2016.01)
(Continued)

(52) U.S. Cl.
CPC .............. H04S 7/303 (2013.01); A61B 34/35 (2016.02); G16H 40/63 (2018.01);
(Continued)

(58) Field of Classification Search
CPC .. H04S 7/303; H04S 2400/11; H04S 2400/15; A61B 34/35; A61B 2034/302; G16H 40/63
(Continued)

(56) References Cited

U.S. PATENT DOCUMENTS

2013/0051560 A1 2/2013 Ray et al.
2016/0026253 A1 1/2016 Bradski et al.
2018/0300940 A1* 10/2018 Sakthivel ................ G06F 3/013

FOREIGN PATENT DOCUMENTS

WO WO-2016191298 A1 12/2016

OTHER PUBLICATIONS

International Search Report and Written Opinion for Application No. PCT/US2020/045380, dated Nov. 11, 2020, 14 pages.
(Continued)

Primary Examiner — Paul Kim
(74) Attorney, Agent, or Firm — Haynes & Boone, LLP.

(57) ABSTRACT

System and method for projecting audio signals to an operator of a teleoperational surgical system to convey spatial orientation associated with the audio signals to the operator. Characteristics of the audio signals such as direction and volume may be selected to give the impression that the remote operator is positioned locally next to the patient. Characteristics of the audio signals may also be modified to provide spatial translations between actual locations of audio sources within a physical audio environment and simulations locations of the audio sources with a virtual audio environment.

20 Claims, 9 Drawing Sheets

(51) Int. Cl.
  *G16H 40/63* (2018.01)
  *A61B 34/30* (2016.01)
(52) U.S. Cl.
  CPC ..... *A61B 2034/302* (2016.02); *H04S 2400/11* (2013.01); *H04S 2400/15* (2013.01)
(58) Field of Classification Search
  USPC .......................................................... 381/303
  See application file for complete search history.

(56) References Cited

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

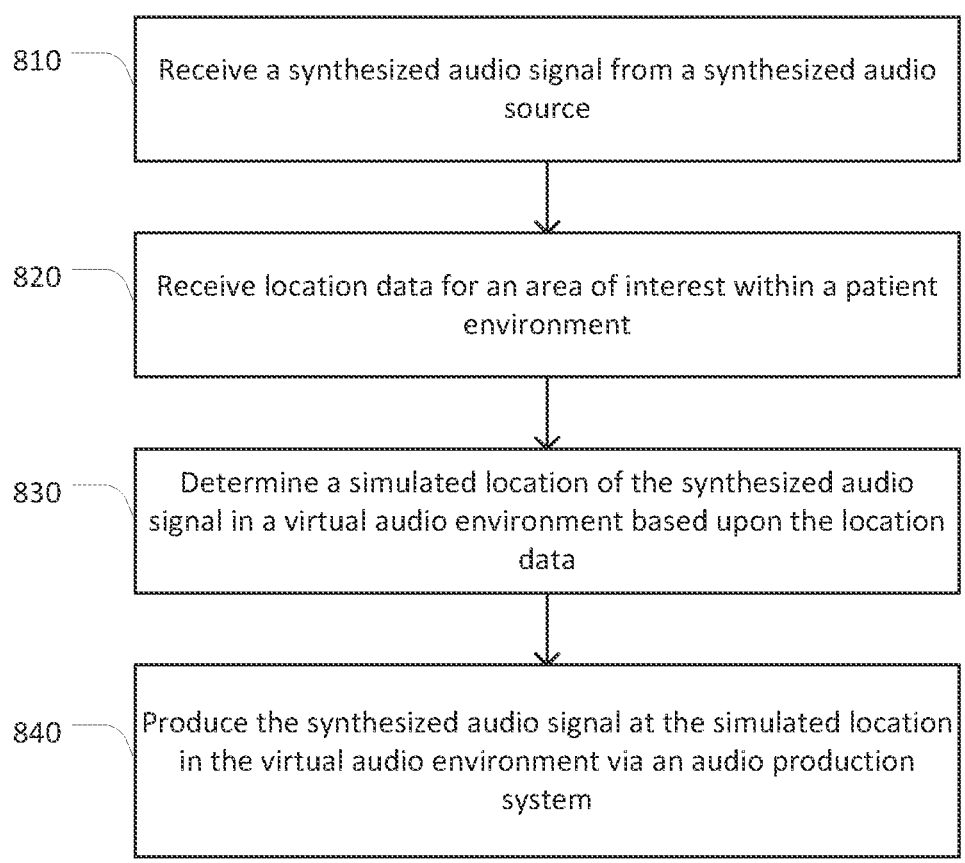

SYSTEM AND METHOD FOR AUDIO SIGNAL PLACEMENT AND PROJECTION

CROSS-REFERENCE TO RELATED APPLICATIONS

This application is a U.S. National Stage patent application of International Application No. PCT/US2020/45380 filed Aug. 7, 2020, which designated the U.S. and claims priority to and the benefit of U.S. Provisional Application 62/889,086 filed Aug. 20, 2019, all of which are incorporated by reference herein in their entireties.

TECHNICAL FIELD

The present disclosure is directed to systems for placing and/or projecting audio signals and more particularly to a system with intelligent audio placement and/or projection.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. Examples of medical teleoperational systems include the da Vinci® Surgical System and the da Vinci® S™ Surgical System from Intuitive Surgical, Inc., of Sunnyvale, Calif. Each of these systems includes a surgeon's console, a manipulator assembly, a high performance three-dimensional ("3-D") vision system, and one or more medical instruments coupled to the manipulator assembly.

During a medical procedure, communication may occur between an operator of a teleoperational system and people in the vicinity of a patient of the teleoperational system. For example, the operator may desire to send instructions to medical personnel in the vicinity of the patient and/or vice versa. Accordingly, robust communication capabilities may result in safer, more efficient, and overall more successful clinical outcomes for teleoperational systems.

Accordingly, it would be advantageous to provide a system that provides improved communication during a surgical procedure.

SUMMARY

The embodiments of the invention are best summarized by the claims that follow the description.

In an aspect of the present invention, an audio system includes one or more audio sensors, a tracking system, an audio reproduction system, and an audio placement controller coupled to the one or more audio sensors, the tracking system, and the audio reproduction system. The audio placement controller may be configured to perform operations including receiving an audio signal at the one or more audio sensors, receiving tracking data associated with an actual location in a physical audio environment of a source of the audio signal from the tracking system, determining a simulated location of the audio signal in a virtual audio environment, and reproducing the audio signal via the audio reproduction system. At least one characteristic (such as volume or direction) of the reproduced audio signal in the virtual audio environment may be determined based upon a relationship between the actual location and the simulated location.

In an embodiment, the one or more audio sensors (e.g., microphones) may be configured to detect the audio signal in a vicinity of a patient of a medical system. The audio signal may correspond to verbal communication by the patient or personnel in the vicinity of the patient. The audio signal may alternatively correspond to an audio output of a medical monitoring device, such as a hear rate monitor, blood pressure monitor, blood oxygen sensor, etc. Furthermore, the audio signal may correspond to an audio output of the medical system.

In some embodiments, the tracking data may correspond to a tracking device worn by the source of the audio signal or it may be derived from the audio signal. For example, the audio sensors may be used to determine a location of the source based upon the volume of the audio as received at each respective sensor, or via triangulation based on a difference in time at which the audio arrived at each audio sensor.

In some embodiments, the simulated location of the audio signal may be representative of the actual location of the source. For example, if the actual location of the source is 5 feet directly left of an endoscope used as a reference point, the simulated location may be five feet directly left of the operator. In other embodiments, the simulated location of the audio signal may be different from the actual location based on the tracking data. The simulated location may be determined based on one or more attributes of the audio signal. For example, the simulated location may be determined based on a determination that the audio signal is associated with an urgent message or is addressed to a listener of the audio system. This determination may be made based at least in part on a name or keyword stated in the audio or a volume at which the audio is received at the audio sensors. In some instances, the simulated location may be determined using an artificial neural network.

The audio reproduction system may include a stereo sound system, a surround sound system, or headphones worn by a listener of the audio system.

An audio system may further include a synthesized audio source. The audio placement controller may be further configured for receiving a synthesized audio signal from the synthesized audio source, determining a second simulated location of the synthesized audio signal in the virtual audio environment, and emitting the synthesized audio signal, via the audio reproduction system, with a characteristic based upon the second simulated location in the virtual audio environment. The synthesized audio signal may correspond to an audio representation of a physiological process of a patient. This may allow the operator to audibly monitor the physiological process.

In another aspect, an audio system may include a memory and one or more processors coupled to the memory. The one or more processors may be configured to read instructions from the memory and perform operations including receiving an audio signal detected in a vicinity of a patient of a medical procedure, receiving tracking information associated with a source of the audio signal, determining a simulated location of the audio signal in a virtual audio environment, and reproducing the audio signal, via an audio reproduction system, to a remote listener. The audio reproduction system may provide the audio signal with a characteristic (e.g., volume, tone, direction, playback speed, etc.) based upon a spatial relationship between the remote listener and the simulated location in the virtual audio environment.

In another aspect, a method may include receiving an audio signal detected in a vicinity of a patient during a medical procedure performed using a medical system, receiving tracking data associated with a source of the audio signal, determining a simulated location of the audio signal in a virtual audio environment, and reproducing the audio signal, via an audio reproduction system, to an operator of the medical system. At least one characteristic of the reproduced audio signal may be based upon the simulated location in the virtual audio environment.

In yet another aspect, a method includes receiving an audio signal from an operator of a medical system at least one sensor, determining a target associated with the audio signal, the target being located in a vicinity of a patient associated with the medical system, receiving tracking data associated with the target, and reproducing the audio signal, via an audio reproduction system, in the vicinity of the patient. The audio reproduction system may focus the reproduced audio signal toward the target based on the tracking data.

In another aspect of the present disclosure, an audio system includes at least one speaker, a synthesized audio source, and an audio placement controller coupled to the synthesized audio source. The audio placement controller may be configured to perform operations including receiving a synthesized audio signal from the synthesized audio source, receiving location data associated with the synthesized audio signal, determining a simulated location of the synthesized audio signal in a virtual audio environment based upon the location data, and emitting the synthesized audio signal via the at least one speaker. At least one characteristic of the emitted audio signal in the virtual audio environment may be determined based upon the location information.

In some embodiments, the synthesized audio signal may correspond to a physiological process of a patient. The physiological process may include at least one of breathing, a heartbeat, blood flow, or any other suitable process. In other embodiments, the synthesized audio signal may correspond to an area of interest within an anatomy of the patient. The simulated location may correspond to a spatial relationship between a field of view displayed for an operator and an actual location of the area of interest.

In some embodiments, an audio system may also include an imaging system. The area of interest may be detected by the imaging system. The imaging system may include a camera disposed within the anatomy of the patient. The imaging system may alternatively include an ultrasound probe, a CT scanner, an X-ray machine, or an MRI machine. A tracking system may register the spatial relationship between the field of view and a reference point of the imaging system. The tracking system may provide the location data to the audio placement controller.

In some embodiments, the at least one speaker may be a directional speaker. The at least one characteristic may include a selection of a direction in which the synthesized audio is emitted from the directional speaker. The at least one speaker may also include at least two speakers. The at least one characteristic may include a selection of at least one speaker of the at least two speakers from which the synthesized audio is emitted. The selection may be based upon a first direction associated with the spatial relationship and a second direction associated with a second spatial relationship between the operator and the at least one speaker. In some embodiments, it may be desirable for the spatial relationships to be identical or similar.

The area of interest may include at least one of arrival of an instrument at a desired location within the anatomy, arrival of an instrument at an undesired location with the anatomy, identification of a foreign object, or bleeding.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 8 is a simplified diagram of a method for producing audio signals according to some embodiments.

DETAILED DESCRIPTION

Figure 1:
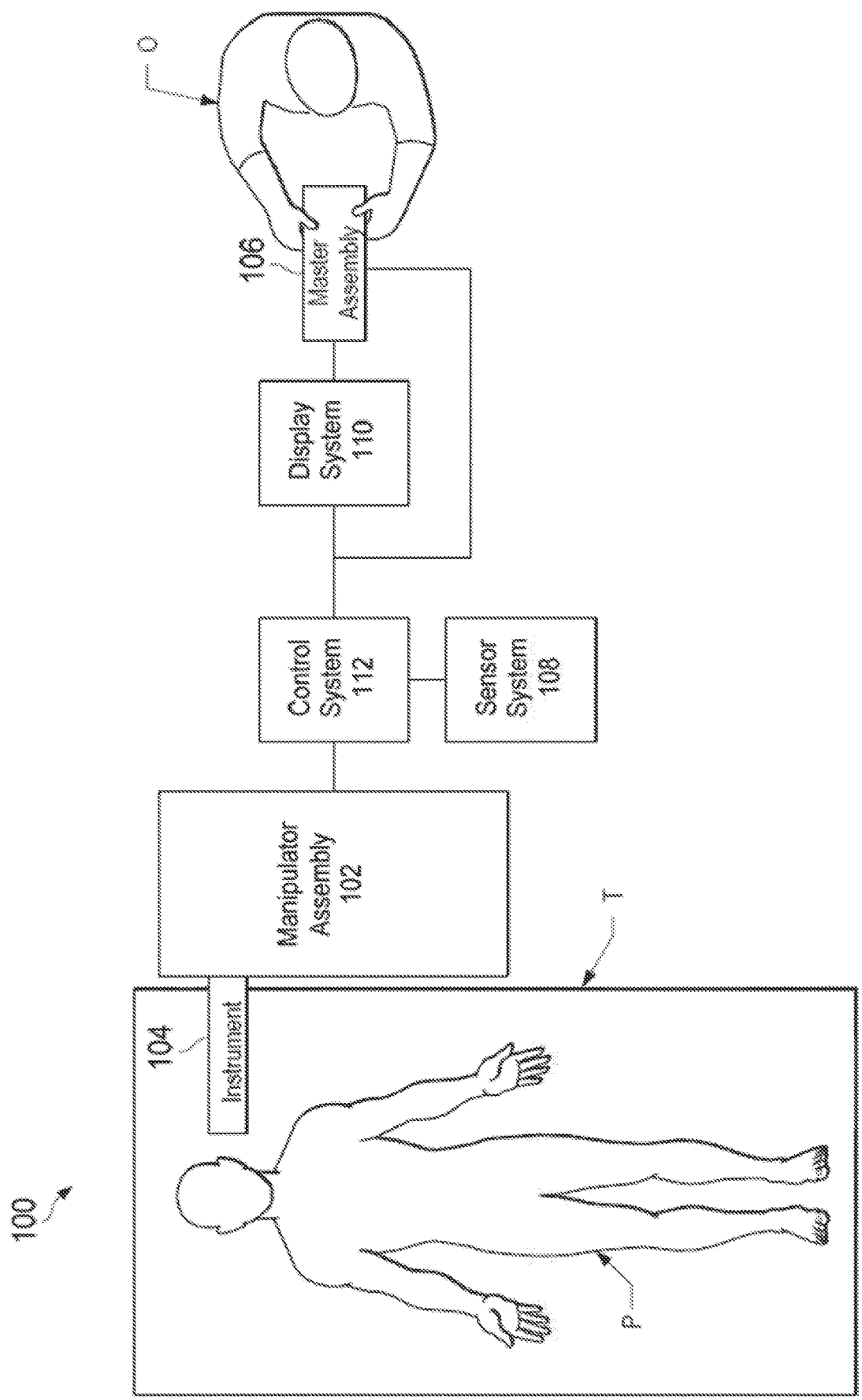
FIG. 1 is a simplified diagram of a teleoperated medical system, in accordance with embodiments of the present disclosure.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" refers to the position of an object or a portion of an object in at least one degree of translational freedom, and to the orientation of that object or that portion of that object in at least one degree of rotational freedom. For an asymmetric, rigid body in a three-dimensional space, a full pose can be described with six total degrees of freedom.

Also, although some of the examples described herein refer to surgical procedures or tools, or medical procedures and medical tools, the techniques disclosed apply to non-medical procedures and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument 104 in performing various procedures on a patient P. Manipulator assembly may be teleoperated or may include both teleoperational and non-teleoperational sub-assemblies for manual, robotic, and/or teleoperated control of medical instrument 104. Manipulator assembly 102 is mounted to or near an operating table T. An operator input system such as a master assembly 106 allows an operator O (e.g., a surgeon, a clinician, or a physician as illustrated in FIG. 1) to view the interventional site and to control manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Manipulator assembly 102 or more specifically the teleoperational manipulator may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system, which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104.

However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112. The processors of the control system 112 may execute instructions corresponding to methods and operators described herein.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 with the hand control as if viewing the workspace in substantially true presence. By true presence, it is meant that the presentation of an image is a true perspective image simulating the viewpoint as if the operator is physically manipulating medical instrument 104 by hand rather than through the teleoperated medical system 100.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of image guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter the data points. In some embodiments, a virtual navigational image may be presented in the display 110 that depicts a model of an anatomical passageway from a perspective of an instrument being inserted along or through a corresponding actual anatomical passageway.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

In general, audio communication is a useful mechanism for conveying information between the vicinity of patient P and operator O during a surgical procedure. Accordingly, a medical system, such as teleoperated medical system 100, may detect audio signals from the vicinity of patient P and reproduce the audio signals for operator O. However, a number of audio sources may be present near patient P during the surgical procedure, in which case it may be difficult for operator O to distinguish among the audio sources and/or understand the context of the audio signal. For example, when a number of medical personnel are located near patient P, it may be difficult for operator O to determine who is speaking, who the speaker is addressing, and/or the like. Likewise, operator O may be visually immersed in the operator's console and may lack visual cues to accompany audio signals provided through speakers at the console.

Accordingly, it is generally desirable to detect and convey spatial relationships among the various audio sources when reproducing audio signals for operator O. Recreating the spatial relationships accurately and/or realistically (i.e., by recreating each audio signal from a position that directly corresponds to the physical location of an audio source) is one possible approach, but further enhancements may be possible. For example, once the location of the various audio sources is determined, each audio source may be mapped to a simulated location, which may or may not match the physical location of the audio source. In this manner, it may be possible to artificially alter the perceived location of high priority audio signals (e.g., urgent messages and/or audio addressed directly to operator O) close to the listener and similarly locate low priority audio signals (e.g., side conversations among medical personnel) further away from the listener.

Figure 2:
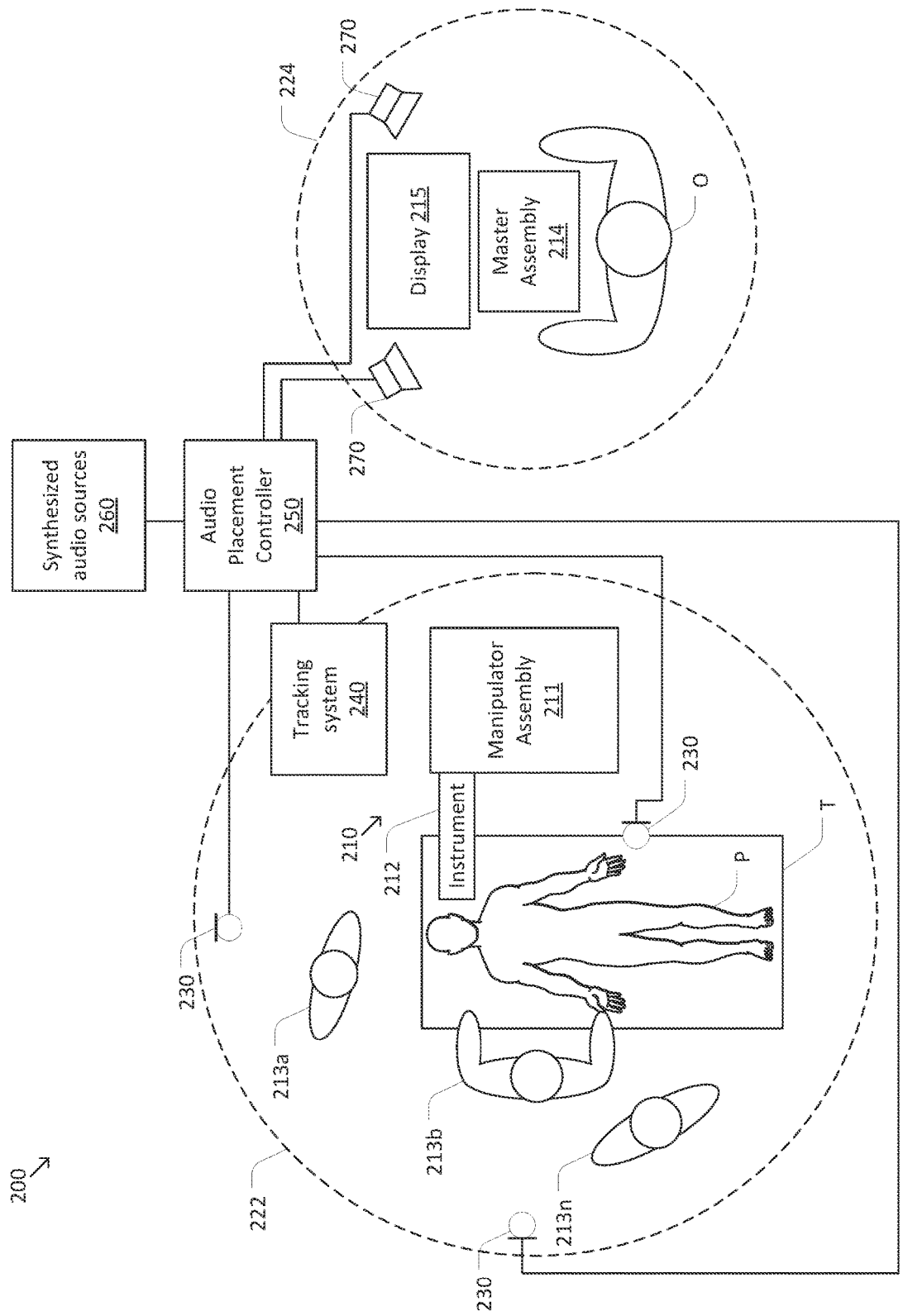
FIG. 2 is a simplified diagram of an audio system with intelligent audio signal placement according to some embodiments.

FIG. 2 is a simplified diagram of an audio system 200 with intelligent audio signal placement according to some embodiments. In some embodiments, audio system 200 may be associated with and/or incorporated into a medical system 210, such as teleoperated medical system 100. Consistent with such embodiments, medical system 210 may include and/or be associated with a patient P, an operating table T, a manipulator assembly 211, and one or more medical instruments 212, which generally correspond to similarly labeled features of FIG. 1. As depicted in FIG. 2, patient P, operating table T, manipulator assembly 211, and medical instrument 212 are located in a vicinity of a patient within a patient environment or patient frame of reference 222. In illustrative embodiments, patient environment 222 may correspond to an operating room. In some embodiments, various personnel 213a-n (e.g., physicians, surgeons, nurses, and/or the like) may be located within the patient environment 222 when performing a surgical procedure.

In some embodiments, medical system 210 may further include and/or be associated with an operator O, a master assembly 214, and a display system 215, which generally correspond to similarly labeled features of FIG. 1. One of the medical instruments 212 may have a visualization system which may include a viewing scope assembly (e.g., an endoscope) that records a concurrent or real-time image of a surgical field of view and provides the image of the field of view to the operator or operator O through the display 215. The image of the field of view on the display 215 contributes to the spatial awareness of the operator O of the patient environment 222.

As depicted in FIG. 2, operator O, master assembly 214, and display system 215 are located in an operator environment or operator frame of reference 224. In illustrative embodiments, operator environment 224 may correspond to a room physically separated from patient environment 222. However, it is to be understood that operator environment 224 and patient environment 222 may be located in the same room and/or may overlap with one another.

In some embodiments, audio system 200 may include one or more audio sensors 230 located in and/or near patient environment 222. In general, audio sensors 230 detect various audio signals that arise from and/or are audible within patient environment 222. Exemplary audio signals include speaking among personnel 213a-n, speaking between personnel 213a-n and patient P, sounds associated with monitoring equipment (e.g., the audio output of a heart rate monitor), ambient noise, and/or the like. In some embodiments, audio sensors 230 may have fixed locations (e.g., microphones mounted to walls, operating table T, manipulator assembly 211, and/or the like) and/or dynamic locations (e.g., microphones clipped to personnel 213a-n and/or patient P) within patient environment 222.

Audio system 200 may also include a tracking system 240 located in and/or near patient environment 222. In some embodiments, tracking system 240 may determine the location of the various audio sources within patient environment 222. For example, tracking system 240 may collect location information associated with personnel 213a-n, patient P, monitoring equipment, and/or any other sources of audio picked up by audio sensors 230. In some embodiments, tracking system 240 may use RFID-based tracking, in which personnel 213a-n are tracked using RFID tags (and/or any other suitable tracking device). In some embodiments, tracking system 240 may include one or more cameras and/or image processors to locate the audio sources using image processing techniques. In some embodiments, tracking system 240 may perform audio signal processing to locate the audio sources based on the audio signals detected by audio sensors 230 (e.g., using triangulation techniques based on arrival time or the relative strength of the audio signals detected by multiple audio sensors 230).

Audio system 200 may further include an audio placement controller 250 that receives audio signal data from audio sensors 230 and/or tracking data from tracking system 240. In some embodiments, audio placement controller 250 may include one or more processors to process the received audio signals and tracking data. According to some embodiments, audio placement controller 250 may map the received audio signals into a virtual audio environment based on the tracking data. In general, the virtual audio environment is an audio environment provided to the operator, who located in the operator environment 224, in which the perceived location and/or directionality from which audio signals originate may be arranged to correspond with the operator's field of view of the patient environment 222. More specifically, audio placement controller 250 may place each audio source at a simulated location within the virtual audio environment based on actual and/or desired spatial positions of the various audio sources relative to the listener (e.g., the operator).

In some embodiments, audio placement controller 250 may perform a direct mapping between the physical location of the audio source (as indicated by the tracking data) in the patient environment 222 and the simulated location of the audio source in the virtual audio environment. That is, the physical location and the simulated location may unaltered and correspond to the same location. However, in some embodiments, the simulated location may be different from the physical location. In some embodiments, audio placement controller 250 may alter the placement of the audio source (as compared to the physical location) in the virtual audio environment based on one or more attributes of the audio signals. For example, audio placement controller 250 may determine that one of personnel 213a-n is speaking with particular urgency (e.g., based on the speaker's loudness, pitch, tone, and/or the like). Consequently, audio placement controller 250 may place the speaker at a simulated location close to the listener in the virtual audio environment to ensure that the urgent message receives appropriate attention.

In addition to placing the audio sources in the virtual audio environment, audio placement controller 250 may set and/or adjust other attributes of the audio signals. For example, audio placement controller 250 may adjust the frequency and/or playback speed of an audio signal based on the tracking data and/or other attributes of the audio signal. In an illustrative embodiment, when the tracking data indicates that an audio source is currently in motion, audio placement controller 250 may adjust the frequency of the corresponding audio signal to enhance (and/or reduce) the Doppler effect caused by the motion.

In some embodiments, audio placement controller 250 may receive synthesized audio signals from one or more synthesized audio sources 260. In some embodiments, the synthesized audio signals may not correspond to actual audio signals picked up by audio sensors 230, but rather may be artificially generated. For example, the synthesized audio signals may correspond to audio representations of physiological processes (e.g., heartbeat, breathing, and/or the like), alerts, notifications, and/or the like.

In some embodiments, audio placement controller 250 may receive audio signals from various other sources in addition to audio sensors 230 and/or synthesized audio sources 260. For example, audio placement controller 250 may receive verbal communication from remote personnel (not shown in FIG. 2) and may place the remote personnel within the virtual audio environment. Consequently, audio placement controller 250 may combine audio signals from a number of sources and/or channels and map them to desired locations within the virtual audio environment.

Audio system 200 further includes an audio reproduction system 270 located in and/or near operator environment 224. Audio reproduction system 270 receives an output signal from audio placement controller 250 and generates an audio output with the desired spatial and/or directional characteristics corresponding to the virtual audio environment. In some embodiments, audio reproduction system 270 may include a stereo sound system, a surround sound system, headphones, and/or the like. In this manner, audio reproduction system 270 may provide operator O with the impression that each audio signal of the virtual audio environment arises from the simulated location within virtual audio environment.

Figure 3A:
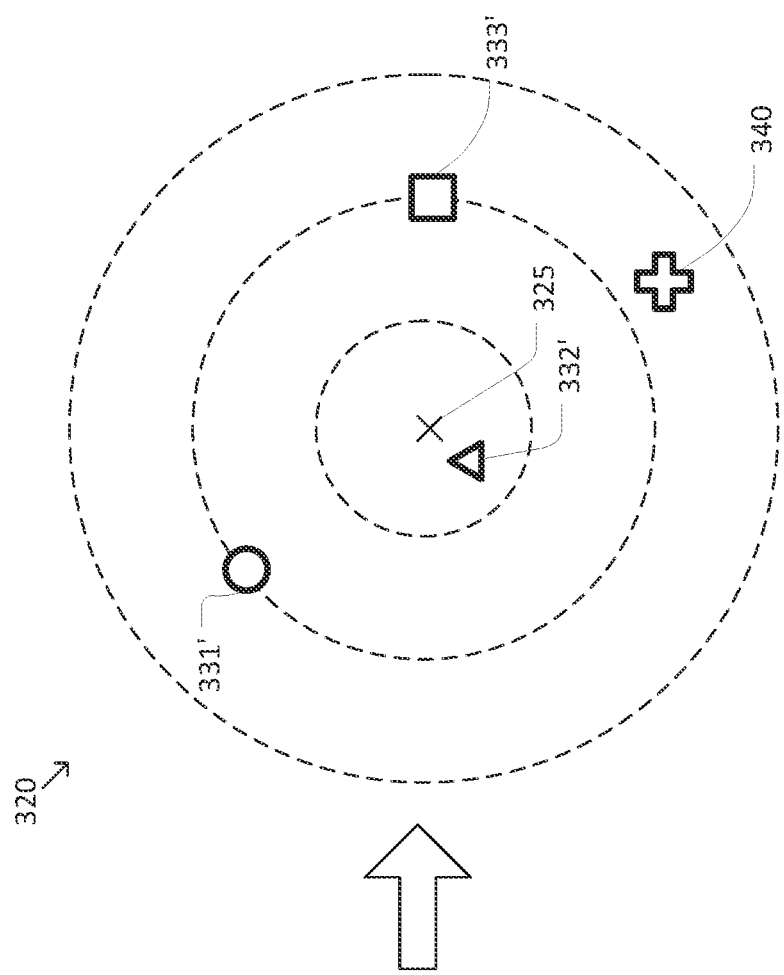
FIG. 3A is a simplified diagram of a transformation between a physical audio environment and a virtual audio environment according to some embodiments.
Figure 3A:
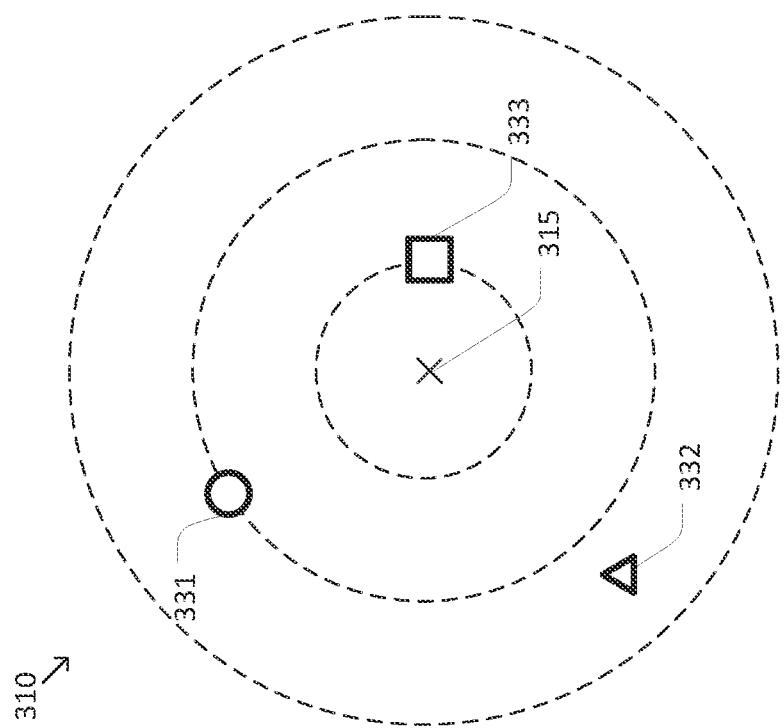

FIG. 3A is a simplified diagram of a transformation between a physical audio environment 310 (e.g., the patient environment 222) and a virtual audio environment 320 according to some embodiments. In some examples consistent with FIG. 2, the transformation may be performed using a controller, such as audio placement controller 250, that receives audio signal data and tracking data. Although physical audio environment 310 and virtual audio environment 320 are represented in two dimensions in FIG. 3A, it is to be understood that the location of audio sources may additionally or alternately be represented in one dimension and/or in three dimensions.

As depicted in FIG. 3A, physical audio environment 310 includes three audio sources 331-333 located at various positions relative to a center location 315. In general, center location 315 may correspond to an arbitrary point, but may correspond to a defined location (e.g., the center of an operating room, the location of a patient, the location of a medical instrument, the location of an imaging system establishing the operator's field of view, and/or the like). Audio sources 331-333 may include virtually any source of audio that may arise in a surgical setting, such verbal communication among medical personnel (e.g., personnel 213a-n), a patient monitoring device, ambient noise, and/or the like.

Virtual audio environment 320 includes three audio sources 331'-333' corresponding to audio sources 331-333. In some embodiments, virtual audio environment 320 may include one or more synthesized audio sources 340 that do not correspond to any of audio sources 331-333. As discussed previously with reference to FIG. 2, synthesized audio source 340 may correspond to a physiological process (e.g., a heartbeat, breathing, and/or the like), an alert, and/or the like. Display systems such as display system 215 may be utilized to convey a multitude of statistics, statuses, configurations, etc., to an operator such that displays may become cluttered with an overwhelming amount of information. Such information may be difficult for an operator to process while also maintaining focus on manipulation of the instrument(s). In this regard, it may be advantageous to provide certain information to the operator audibly rather than visually at least for the sake of reducing an excessive amount of distracting information provided by the display system 215. Synthesized audio source 340 may provide such audible information.

Audio sources 331'-333' and 340 are placed at simulated locations relative to a listener location 325. In some embodiments, the listener location 325 may correspond to the location of the operator's field of view. As listener location 325 may be positioned in the center of virtual audio environment 320, the listener (e.g., operator O) located at listener location 325 will perceive audio signals from audio sources 331'-333' and 340 as originating from their respective locations in virtual audio environment 320.

As depicted in FIG. 3A, the locations of audio sources 331'-333' may or may not match the locations of audio sources 331-333 in the physical audio environment 310. For example, audio source 331' is placed in approximately the same location in the virtual audio environment 320 as in the physical audio environment 310. As another example, audio source 332' is significantly more centrally located in virtual audio environment 320 than corresponding audio source 332 is in physical audio environment 310, whereas audio source 333' is farther from the center in virtual audio environment 320 than in physical audio environment 310. These virtual placements may be accomplished, for example, by increasing the volume of audio from audio source 332, reducing noise in the signal from audio source 332, changing a pitch, speed, or other audio characteristic of the audio from audio source 332, and/or reducing the volume of the other audio sources. There may be a variety of reasons to artificially move audio source 332' close to the listener in virtual audio environment 320. For example, when audio source 332 may correspond to a member of the medical team speaking with unusual urgency. In another example, the member of the medical team may state a keyword and/or key phrase (e.g., the operator's name) indicating that he or she desires to address operator O directly. Consequently, placing audio source 332' at a central location close to the listener may help convey to operator O the impression that the team member is addressing operator O directly.

Figure 3B:
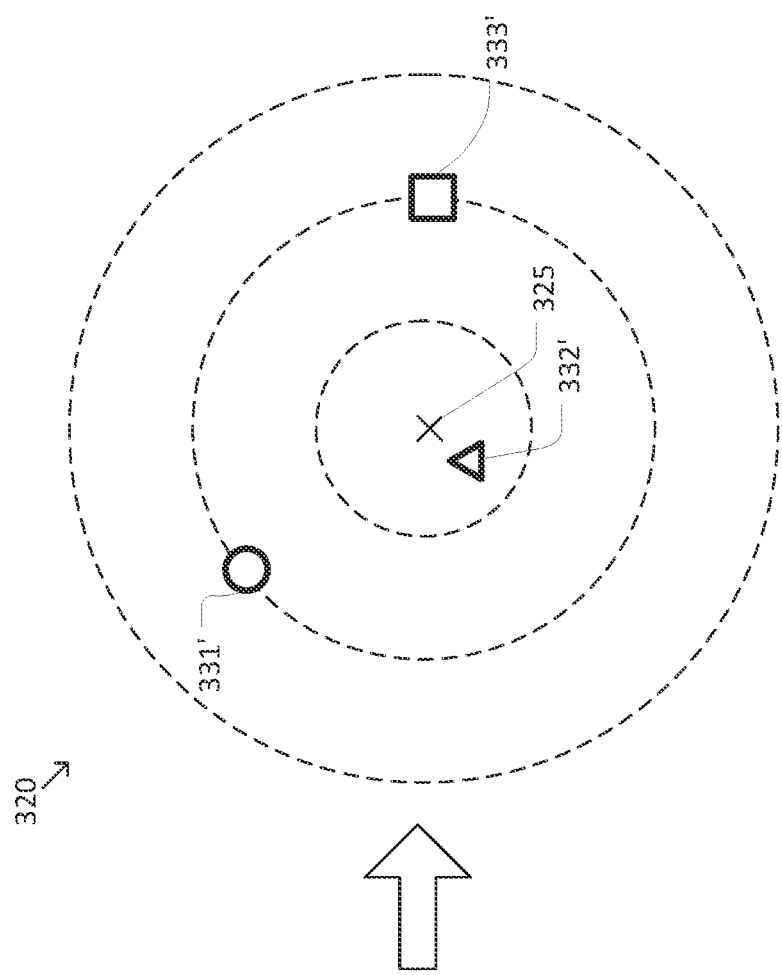
FIG. 3B is a simplified diagram of a transformation between the physical audio environment and virtual audio environment of FIG. 3A at a different point in time according to some embodiments.
Figure 3B:
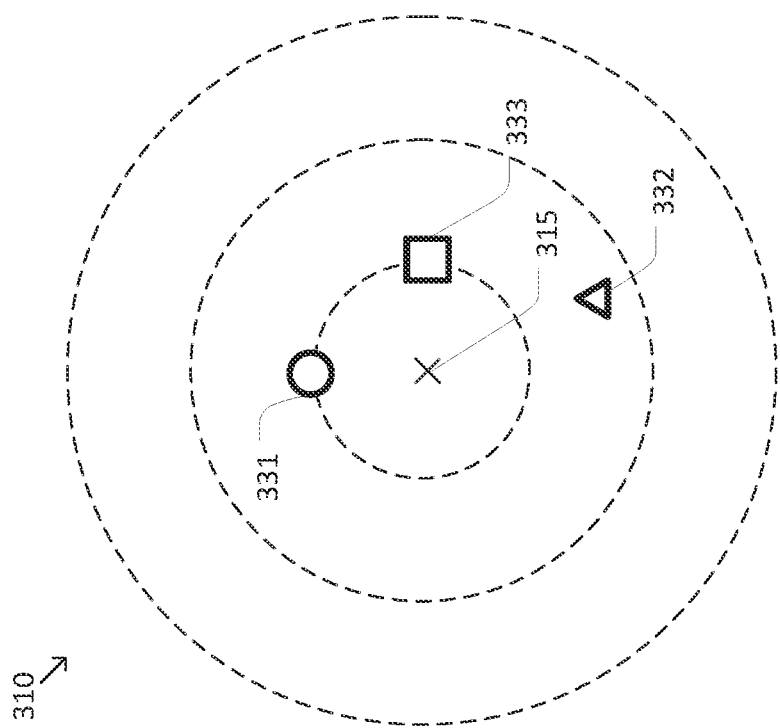

Furthermore, it may be desirable to translate the dynamic actual positions of audio sources 331-333 to static virtual positions of audio sources 331'-333'. In other words, personnel or equipment may be moving around the physical audio environment 310 during a surgical operation, as illustrated by the differences between FIG. 3A at a first point in time and FIG. 3B at a different moment in time, but the operator O may be unaware of their movements due to the operator's focus being trained on the display system. In order to maintain an understanding of who is speaking based on directional cues in the virtual audio environment 320, the virtual locations of audio sources 331'-333' in the virtual audio environment 320 may be kept stationary while the respective actual audio sources 331-333 move about the room as shown by their changed locations between FIG. 3A and FIG. 3B. That is, even as audio source 332 (which may be, e.g., a nurse) moves from the left side of center location 315 (e.g., a manipulator assembly) to the right side, sound from the audio source may be directed to the operator (disposed at the center location 325 of the virtual audio environment) from a common angle, such as only from a speaker on the operator's left side, to create the impression that the audio source 332 is stationary at the operator's left side. This may enable the operator to distinguish audio feedback from that particular audio source 332 from that of other audio sources 331 and 333.

A variety of techniques may be utilized to generate the virtual audio environment by mimicking properties of the physical audio environment and/or modifying certain properties thereof. For example, to mimic the physical audio environment in a manner which gives the operator the impression they are located in the center of it, directions and volumes of various sounds (alarms, voices, tools, etc.) may be detected in the physical audio environment and recreated in the virtual audio environment with properties similar to those occurring at the simulated location of the operator (e.g., center of the physical audio environment). By replicating the properties of the various sounds in a manner similar or identical to those occurring at that the simulated location, the operator may receive audio information as if the operator is actually present at the simulated location, creating the impression that the operator is present at that simulated location (such as standing over the patient or standing at the location of the imaging system generating the operator's field of view).

Additionally, properties of sounds may be modified within the virtual audio environment to give the operator impressions distinct from those actually occurring at a simulated location. That is, the sounds provided to the operator may be modified to enhance or supplement the real-world audio using tracking system 240, audio placement controller 250 and synthesized audio sources 260 of FIG. 2. Contemplated techniques for modifying sound in the virtual audio environment include, for example, increasing the volume and/or changing a direction of one or more voices as discussed above. In this regard, the virtual location of a nurse, for example, may be brought into close proximity to the operator by increasing the volume of the nurse's voice, whereas in the physical audio environment the nurse may be distant from the operator making the nurse difficult to hear. In contrast, the volumes of other voices may be reduced, such as chatter between medical students or other observers in a gallery. In this regard, the audio system may determine the observers are not active participants in the operation based upon their location in the room or may determine their comments are unnecessary based upon the volume at which they are spoken. Accordingly, the audio system may filter their voices out of the virtual audio environment completely to avoid distracting the operator. As another contemplated technique, the volume of ambient noise such as tools and equipment (e.g., ventilator) operating may be decreased.

Yet another contemplated technique for modifying sounds in the virtual audio environment includes reducing echo or reverberation. Operating rooms are typically characterized with smooth rigid surfaces such as tile floors and stainless-steel tables. These surfaces may reflect sound waves, contributing to background noise which is distracting to an operator and may interfere with other, more important sounds. Accordingly, the audio system 200 may reduce the volume of or eliminate reflected sound waves from the physical audio environment 310 when generating an audio signal for the virtual audio environment 320 by filtering out duplicative wave patterns associated with reflection and reverberation.

Another contemplated technique includes altering content of speech. In other words, certain phrases or comments stated by personnel in the physical audio environment 310 and determined to be unimportant may be omitted from the audio produced in the virtual audio environment 320. For example, when a member of the medical team makes a statement that is addressed to another team member other than the operator, indicated by starting the statement with the team member's name, for example, that portion of audio may not be generated in the virtual audio environment 320. In contrast, portions of the team member's statements that are set-off by the operator's name may be sent through to the virtual audio environment 320. Of course, various combinations of these contemplated techniques and others may be utilized to achieve a desired virtual audio environment 320.

Figure 4:
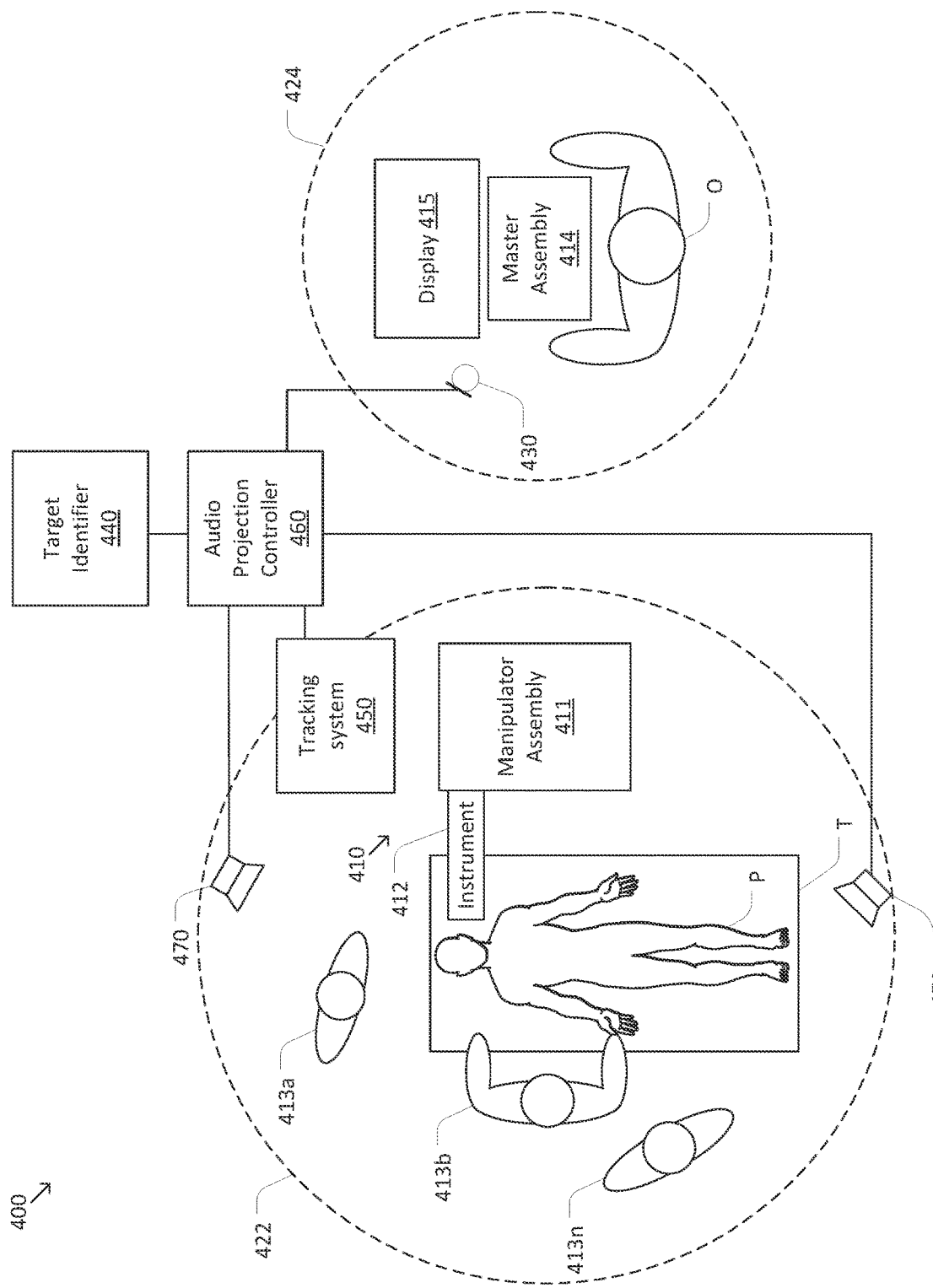
FIG. 4 is a simplified diagram of an audio system with intelligent audio projection according to some embodiments.

FIG. 4 is a simplified diagram of an audio system 400 with intelligent audio projection according to some embodiments. Like audio system 200, audio system 400 addresses the desire for improved audio communication between the vicinity of a patient P and an operator O. In comparison to audio system 200, in which operator O is a listener, audio system 400 is configured for a scenario in which operator O is a speaker. Although audio system 200 and audio system 400 are depicted as separate systems for clarity, it is to be understood that audio system 200 and audio system 400 may be combined to provide two-way audio communication between the vicinity of patient P and operator O.

Like audio system 200, audio system 400 may be associated with and/or incorporated into a medical system 410, such as teleoperated medical system 100. Consistent with such embodiments, medical system 410 may include and/or be associated with a patient P, an operating table T, a manipulator assembly 411, and a medical instrument 412, which generally correspond to similarly labeled features of FIG. 1. As depicted in FIG. 4, patient P, operating table T, manipulator assembly 411, and medical instrument 412 are located in a patient vicinity or environment 422. In illustrative embodiments, patient environment 422 may correspond to an operating room. In some embodiments, various personnel 413a-n (e.g., physicians, surgeons, nurses, and/or the like) may be located within the patient environment 422 when performing a surgical procedure.

In some embodiments, medical system 410 may further include and/or be associated with an operator O, a master assembly 414, and a display system 415, which generally correspond to similarly labeled features of FIG. 1. As depicted in FIG. 4, operator O, master assembly 414, and display system 415 are located in an operator environment 424. In illustrative embodiments, operator environment 424 may correspond to a room physically separated from patient environment 422. However, it is to be understood that operator environment 424 and patient environment 422 may be located in the same room and/or may overlap with one another.

In some embodiments, audio system 400 may include an audio sensor 430 located in and/or near operator vicinity 420. In general, audio sensor 430 is configured to detect verbal communication from operator O. For example, audio sensor 430 may include a microphone clipped to operator O, mounted on and/or built into master assembly 414 and/or display system 415, and/or the like.

In some embodiments, operator O may desire to speak to one or more targets in patient environment 422. For example, operator O may desire to speak to a particular one of personnel 413a-n and/or may desire to speak to patient P. Accordingly, audio system 400 may include a target identifier 440 that identifies one or more targets that operator O intends to address. In some examples, the one or more targets may be manually identified by operator O (e.g., by making a selection via master assembly 414). In some examples, the one or more targets may be identified based on one or more keywords and/or key phrases spoken by operator O (e.g., by saying the target's name). In some examples, the one or more targets may be automatically identified (e.g., by determining likely targets based on the content and/or subject matter of the speech). In some embodiments, one or more audio sensors 430 may be used to determine a target based upon a direction in which the operator O projects the spoken audio. For example, detected volumes at a plurality of audio sensors 430 may be used to identify a target based upon the locations of the personnel 413a-n within the virtual audio environment.

Audio system 400 may also include a tracking system 450 located in and/or near patient environment 422. In some embodiments, tracking system 450 may determine the location of the potential targets within patient environment 422. For example, tracking system 450 may collect location information associated with personnel 413a-n and/or patient P. In some embodiments, tracking system 450 may use RFID-based tracking, in which personnel 413a-n are tracked using RFID tags (and/or any other suitable tracking device). In some embodiments, tracking system 450 may include one or more cameras and/or image processors to locate the potential targets using image processing techniques Audio system 400 may further include an audio projection controller 460 that receives audio signal data from audio sensor 430, target data from target identifier 440, and/or target tracking data from tracking system 450. In some embodiments, audio projection controller 460 may include one or more processors to process the received audio signal data, target data, and target tracking data. According to some embodiments, audio projection controller 460 may determine a projection profile for the audio signal based on the target data and/or the target tracking data. In particular, the projection profile may identify spatial variations in the volume, frequency, and/or other attributes of the audio signal such that the audio signal reaches the intended target.

Audio system 400 also includes an audio reproduction system 470 located in and/or near patient environment 422. Audio reproduction system 470 receives an output signal from audio projection controller 460 and reproduces an audio output with the desired spatial and/or directional characteristics corresponding to the projection profile. In some embodiments, directional audio reproduction system 470 may include a directional speaker system, headphones worn by personnel 413a-n, a set of speakers arranged in different locations within patient environment 422, and/or the like. In this manner, audio reproduction system 470 allows operator O to address a particular target within patient environment 222 without creating an auditory distraction for non-targets.

Figure 5:
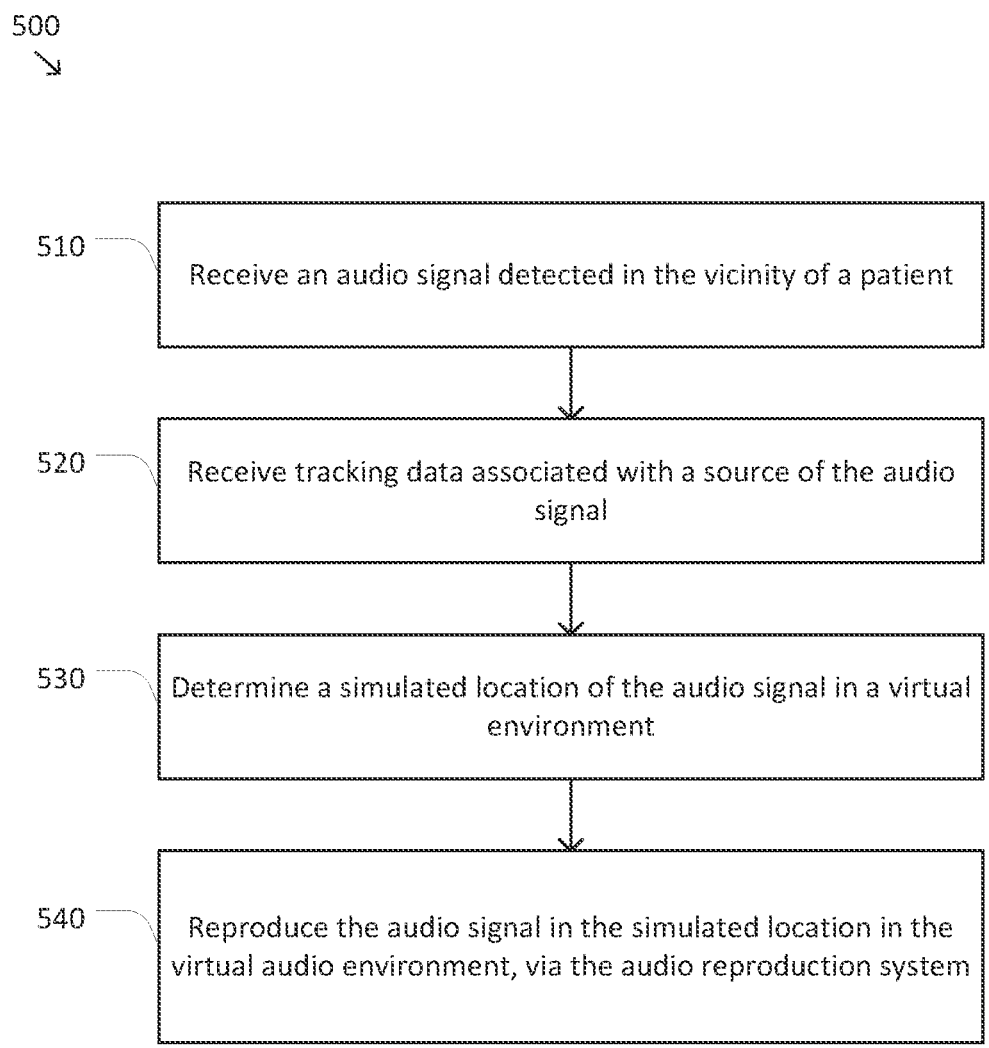
FIG. 5 is a simplified diagram of a method for placing audio signals according to some embodiments.

FIG. 5 is a simplified diagram of a method 500 for placing audio signals according to some embodiments. According to some embodiments consistent with FIG. 2, method 500 may be performed by a controller of an audio system, such as audio placement controller 250, during a medical procedure. In some embodiments, method 500 may allow an operator of a medical system used in the medical procedure to listen to audio signals arising from a vicinity of a patient of the medical procedure.

At a process 510, an audio signal detected in the vicinity of the patient is received. In some embodiments, the audio signal may correspond to verbal communication from the patient of the medical procedure, verbal communication from personnel in the patient vicinity, audio output by patient monitoring equipment (e.g., heart rate monitors), audio output by the medical system, ambient noise, and/or the like. In some embodiments, the audio signal may be received from microphones (and/or other suitable audio transducers) placed in and/or near the patient vicinity (e.g., in the operating room with the patient).

At a process 520, tracking data associated with a source of the audio signal is received. As indicated previously, the source of the audio signal may correspond to the patient, personnel located in the patient vicinity, patient monitoring equipment, the medical system, and/or the like. In some embodiments, the tracking data may identify a relative and/or absolute location of the source within the patient vicinity. In some embodiments, the tracking data may correspond to RFID tracking data based on RFID tags (and/or any other suitable tracking devices) worn by the personnel in the patient vicinity. In some examples, the tracking data may be derived from the received audio signal, e.g., by triangulating the location of the source based on the strength of the audio signal.

At a process 530, a simulated location of the audio signal in a virtual audio environment is determined. The simulated location of the audio signal may be relative to the listener location in the virtual audio environment. In some embodiments, the simulated location may match the physical location of the audio signal as indicated by the tracking data. In other words, a direct mapping occurs between the physical location of the audio signal (as indicated by the tracking data) in the patient environment 222 and the simulated location of the audio source in the virtual audio environment. In some embodiments, the simulated location may not match the physical location of the audio signal as indicated by the tracking data. In other words, an altered mapping of the tracking data for physical location of the audio signal in the patient environment 222 is performed. The altered mapping creates a simulated location of the audio source in the virtual audio environment that is different from physical location of the audio signal in the patient environment 222. In some embodiments, the simulated location of the audio source in the virtual audio environment is based upon a spatial relationship to the listener location. For example, the simulated location may be determined based on one or more attributes of the audio signal (e.g., the tone, the content of the verbal communication, keywords and/or key phrases included in the verbal communication, and/or the like). In this manner, high priority audio signals (e.g., urgent messages, messages addressed directly to the listener, and/or the like) may be artificially placed close to the listener, whereas low priority audio signals (e.g., ambient noise, conversations that do not involve the listener, and/or the like) may be artificially placed far from the listener. In some examples, the simulated location may be determined using machine learning techniques. For example, an artificial neural network may be developed and trained to predict a desired simulated location of the audio signal based on the tracking data, the attributes of the audio signal, and/or a variety of other factors that may influence the desired simulated location. In addition to determining the simulated location of the audio signal, other attributes of the audio signal may be selected at process 530. For example, the frequency, playback speed, and/or other attributes may be adjusted. More generally, various audio and/or spatial properties of the audio signal may be manipulated as desired to create a desired audio impression on the listener.

At a process 540, the audio signal is reproduced, via an audio reproduction system, to provide a listener (e.g., a remote listener positioned outside of the patient vicinity, such as the operator of the medical system) with an impression that the reproduced audio signal arises from the simulated location in the virtual audio environment determined at process 530. In some embodiments, the audio reproduction system may correspond to a stereo sound system, a surround sound system, headphones, and/or any other type of audio reproduction system capable of conveying spatial characteristics of the audio signal.

Figure 6:
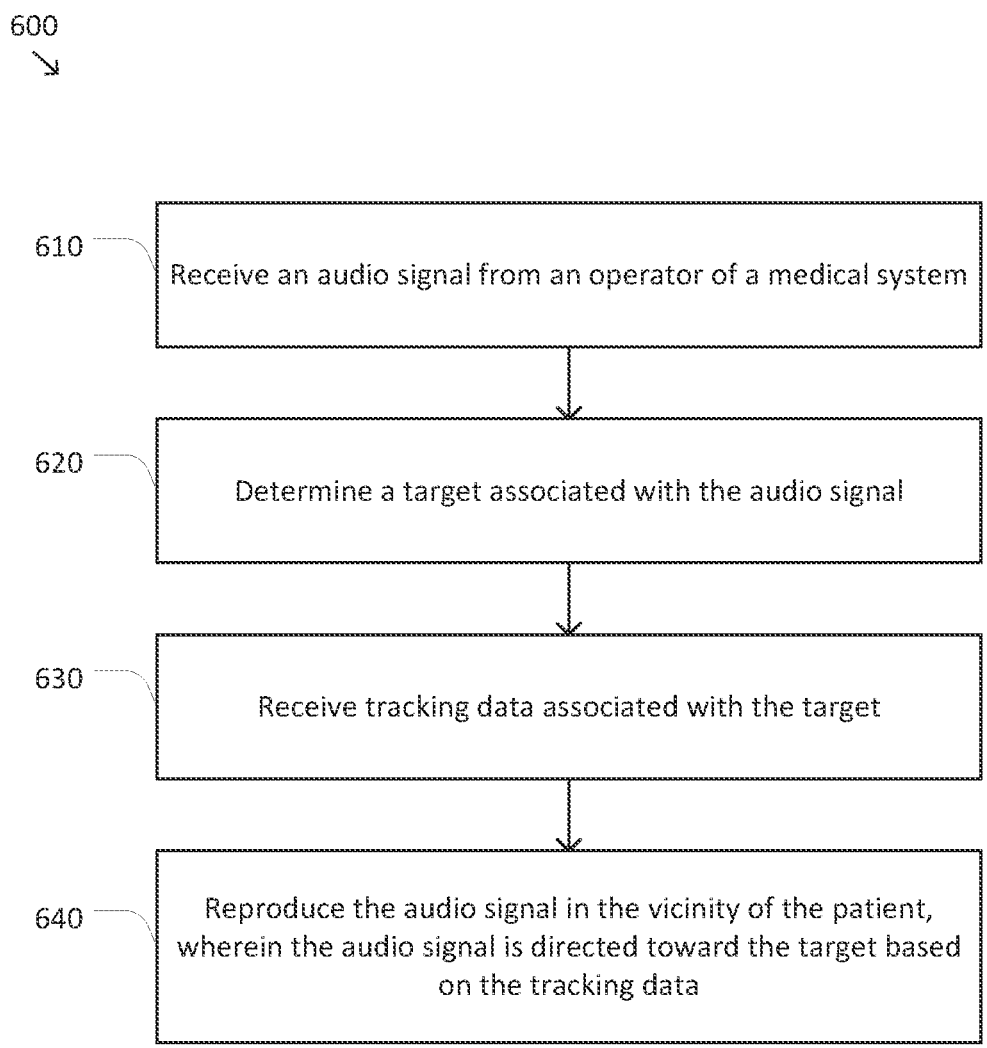
FIG. 6 is a simplified diagram of a method for projecting audio signals according to some embodiments.

FIG. 6 is a simplified diagram of a method 600 for projecting audio signals according to some embodiments. According to some embodiments consistent with FIG. 4, method 600 may be performed by a controller of an audio system, such as audio projection controller 460, during a medical procedure. In some embodiments, method 600 may allow an operator of a medical system used in the medical procedure to transmit audio signals to targeted personnel and/or locations within a vicinity of a patient of the medical procedure.

At a process 610, an audio signal is received from the operator of the medical system. In some examples, the audio signal may correspond to verbal communication received via a microphone located in the vicinity of the operator and/or clipped to the operator. In some examples, the audio signal may be synthesized and/or may correspond to pre-recorded audio received in response to a selection made by the operator via an input interface (e.g., pressing a button to initiate playback of the audio signal).

At a process 620, a target associated with the audio signal is determined. In general, the target corresponds to one or more entities located in the vicinity of the patient. For example, the target may include the patient, personnel in the vicinity of the patient, and/or the like. In some examples, the target may be determined based on a manual input from the operator (e.g., a selection made via the input interface), the content of the audio signal, keywords and/or key phrases included in the audio signal, and/or the like.

At a process 630, tracking data associated with the target is received. As indicated previously, the target of the audio signal may correspond to the patient, personnel located in the patient vicinity, and/or the like. In some embodiments, the tracking data may identify a relative and/or absolute location of the target within the patient vicinity. In some embodiments, the tracking data may correspond to RFID tracking data based on RFID tags (and/or any other suitable tracking devices) worn by the personnel in the patient vicinity. In some examples, the tracking data may be derived from sensor data (e.g., image and/or audio sensor data) collected in the vicinity of the patient.

At a process 640, the audio signal is reproduced, via an audio reproduction system, in the vicinity of the patient. The audio reproduction system directs or focuses the reproduced audio signal on the target based on the tracking data received at process 630. In some embodiments, the audio reproduction system may include a directional sound system, a plurality of speakers distributed in the vicinity of the patient, and/or any other audio reproduction system capable of reproducing the audio signal in a localized manner. In some embodiments, the audio signal may be reproduced with maximum volume at or near the location of the target, whereas the volume elsewhere may be reduced to mitigate noise pollution and/or distraction for non-targets in the vicinity of the patient.

Figure 7:
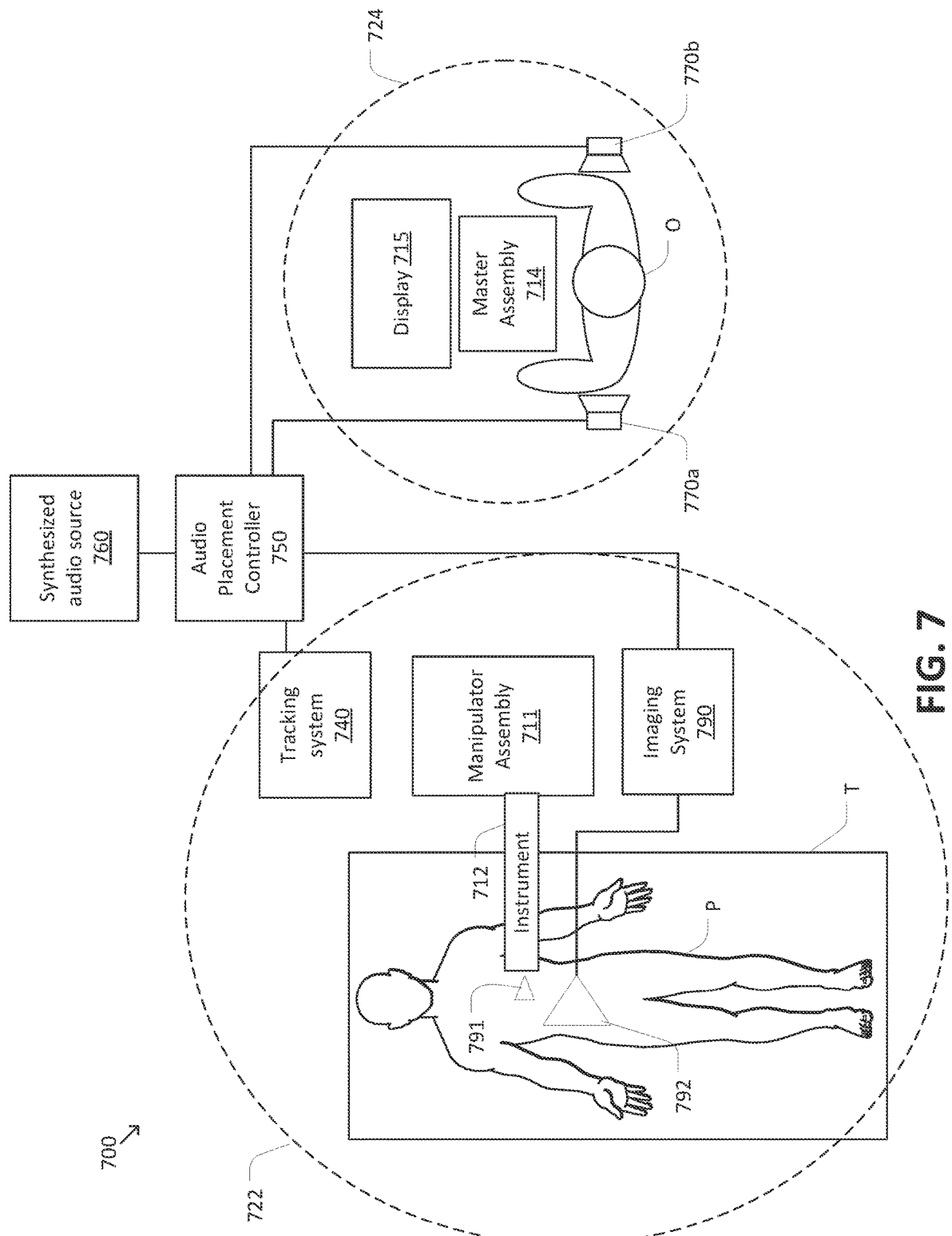
FIG. 7 is a simplified diagram of an audio system with intelligent audio signal placement according to some embodiments.

Turning to FIG. 7, an audio system 70) is shown. An imaging system 790, which may be a supplemental imaging system, may be utilized to capture imagery of internal components of the patient's anatomy. For example, the imaging system 790 may be an endoscope, a camera, an ultrasound probe, a CT scanner, an MRI machine, and X-ray machine, or any other suitable device. Concurrently with the imaging system 790 capturing imagery, the operator O may be operating manipulator assembly 711 (e.g., manipulator assembly 102), and more specifically one or more instruments 712 (which may include, for example, an imaging instrument such as an endoscope or an endoscope/tool combination), via the master assembly 714 and display system 715, located in an operator environment 224. Imaging system 790 may be configured to identify areas with features, conditions, or events of interest within the anatomy of the patient P, within the patient environment 722. For example, excessive bleeding, identification of a foreign object (e.g., a surgical screw), or proximity of an instrument to a particular anatomical feature may be areas about which the operator needs to be aware. However, the endoscopic field of view that is presented to the operator O on the display system 715 from an instrument 712 may not record or capture the area of interest because the event or feature is outside the endoscopic field of view. Accordingly, the imaging system 790 may be operable to detect areas of interest independently from the operator O. The location and orientation of the instrument field of view 791 may be known relative to the instrument system field of view 792. For example, tracking system 740 may determine, register, and track a spatial relationship between the instrument 712 (and more specifically in some instances the field of view 791 of the instrument 712) and a field of view 792 of the imaging system 790. In some embodiments, tracking system 740 may be similar to tracking system 240. In some embodiments, the location of the instrument field of view 791 relative to the imaging system field of view 792 may be known based on a kinematic relationship between the instrument 712 and the imaging system 790. Upon recognizing an area of interest, the tracking system 740 may determine a spatial relationship between the field of view 791 of the instrument 712 or an origination point of the field of view 791 (such as a distal end of an imaging instrument) and the specific location of the area of interest within the field of view 792 of the imaging system.

Based upon the spatial relationship between the area of interest and the field of view 791, the audio placement controller 750 may determine a simulated location of a synthesized audio signal from a synthesized audio source 760. The simulated location may represent the direction of the area of interest (e.g., patient bleeding, at-risk area) outside of and relative to the field of view 791. Synthesized audio source 760 may be an alert generator or other component/software configured to generate an audio alert in response to the recognition of an area of interest. In some embodiments, the synthesized audio source 760 may be part of the imaging system 790, audio placement controller 750, and/or tracking system 740. The simulated location of the synthesized audio signal may be used by audio placement controller 750 to select one or more speakers 770a, 770b of an audio production system through which the synthesized audio signal is emitted. The selection of one or more speakers may include determining a volume at which to play the synthesized audio signal from the one or more speakers. For example, a simulated location that is directly left of the operator in the virtual audio environment (which may correspond to the operator's environment 724) may cause audio placement controller 750 to select only the left speaker 770a at 80 dB, whereas a simulated location that is directly in front of the operator may cause audio placement controller 750 to select both speakers 770a and 770b each at 70 dB. A simulated location between these two directions may result in left speaker 770a playing the synthesized audio signal at 75 dB and the right speaker 770b playing the synthesized audio signal at 65 dB.

In the illustrated embodiment of FIG. 7, an area of interest detected in the field of view 792 of the imaging system 790 is primarily left of the field of view 791 of the instrument 712 (e.g., endoscope). Accordingly, the audio placement controller 750 may determine that the synthesized audio signal comprising an alert to the operator should be emitted primarily from the left speaker 770a to alert or raise the operator's awareness of the area of interest to the left side of the field of view 791 as being viewed by the operator O on the display system 715. This may prompt the operator O to manipulate the instrument 712 to look to the left and view the event or feature of interest.

It should be appreciated that imaging system 790 may not include an endoscope but rather may be a CT scanner, ultrasound probe, etc., the imagery of which may be spatially registered with respect to the instrument 712 by the tracking system 740. Moreover, as the operator O manipulates the endoscope of instrument 712 to overlap field of view 791 with the field of view 792 of the imaging system 790, the display system 715 may superimpose anatomical imagery from the imaging system 790 with the camera view of the instrument 712.

FIG. 8 is a simplified diagram of a method 800 for producing audio signals according to some embodiments. According to some embodiments consistent with FIG. 7, method 800 may be performed by a controller of an audio system, such as audio placement controller 750, during a medical procedure. In some embodiments, method 800 may allow an operator of a medical system used in the medical procedure to experience a virtual audio environment that includes synthesized audio signals that provide directional indication of areas of interest outside of the operator's field of view.

At a process 810, a synthesized audio signal may be received from a synthesized audio source such as synthesized audio source 760. The process 810 may be performed anytime during the method 800, not necessarily prior to the other processes. In some embodiments, the synthesized audio source 760 may be an alert generator or other component/software configured to generate an audio indication associated with an area of interest.

At a process 820, location data for an area of interest within a patient environment may be received. In some embodiments, the area of interest may be an area within a patient anatomy. In some embodiments, the area of interest may be in an area inside the patient that is outside of the field of view (e.g., field of view 791) of the operator's primary imaging system, such as an endoscope. In some embodiments, the area of interest may be detectable, by image processing or other detection techniques, in a field of view (e.g., field of view 792) of a supplemental imaging system. The fields of view of both imaging systems may be registered such that the direction of the location data for the area of interest that is outside of the operator's view is known relative to the operator's field of view.

At a process 830, a simulated location of the synthesized audio signal is determined in a virtual audio environment based on the location data. In some embodiments, the virtual audio environment is an audio environment provided to the operator, who is located in the operator environment 724, in which the perceived location and/or directionality from which the synthesized audio signals originate may be arranged to correspond with the operator's field of view of the patient environment 722.

At a process 840, the synthesized audio signal is produced at the simulated location in the virtual audio environment via the audio production system (e.g. speakers 770a. 770b). In some embodiments, the virtual audio environment is the audio environment experienced by the operator O in the operator environment 724.

Some examples of processors, such as a processor of audio placement controller 250 and/or audio projection controller 460, may include non-transient, tangible, machine readable media that include executable code that when run by one or more processors (e.g., a processor of audio placement controller 250 and/or audio projection controller 460) may cause the one or more processors to perform the processes of methods 500, 600 and/or 800. Some common forms of machine readable media that may include the processes of methods 500 and/or 600 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An audio system, comprising:
   one or more audio sensors;
   a tracking system;
   an audio reproduction system; and
   an audio placement controller coupled to the one or more audio sensors, the tracking system, and the audio reproduction system, wherein the audio placement controller is configured to perform operations comprising:
   receiving an audio signal at the one or more audio sensors;
   receiving tracking data from the tracking system, the tracking data associated with an actual location in a physical audio environment of a source of the audio signal;
   determining a simulated location of the audio signal in a virtual audio environment; and
   reproducing the audio signal in the simulated location in the virtual audio environment, via the audio reproduction system.

2. The audio system of claim 1, wherein the one or more audio sensors are configured to detect the audio signal in a patient environment.

3. The audio system of claim 2, wherein the audio signal corresponds to verbal communication by a patient or personnel in the patient environment.

4. The audio system of claim 2, wherein the audio signal corresponds to an audio output of a patient monitoring device in the patient environment.

5. The audio system of claim 2, wherein the audio signal corresponds to an audio output of a medical system in the patient environment.

6. The audio system of claim 1, wherein the tracking data corresponds to a tracking device attached to the source of the audio signal.

7. The audio system of claim 1, wherein the tracking data is derived from the audio signal.

8. The audio system of claim 1, wherein the simulated location of the audio signal is different from the actual location based on the tracking data.

9. The audio system of claim 1, wherein the simulated location is determined based on one or more attributes of the audio signal.

10. The audio system of claim 1, wherein the simulated location is determined based on a determination that the audio signal is associated with an urgent message or is addressed to a listener of the audio system.

11. The audio system of claim 1, wherein the simulated location is determined using an artificial neural network.

12. The audio system of claim 1, wherein the audio reproduction system includes a stereo sound system, a surround sound system, or headphones worn by a listener of the audio system.

13. The audio system of claim 1, further comprising a synthesized audio source, wherein the operations further comprise:
   receiving a synthesized audio signal from the synthesized audio source;
   determining a second simulated location of the synthesized audio signal in the virtual audio environment; and
   emitting the synthesized audio signal, via the audio reproduction system, with a characteristic based upon the second simulated location in the virtual audio environment.

14. The audio system of claim 13, wherein the synthesized audio signal corresponds to an audio representation of a physiological process of a patient.

15. A system, comprising:
   a memory; and
   one or more processors coupled to the memory, the one or more processors being configured to read instructions from the memory and perform operations comprising:
   receiving an audio signal detected in a patient environment;
   receiving tracking information associated with a location of a source of the audio signal in the patient environment;
   determining a simulated location of the audio signal in a virtual audio environment; and
   reproducing the audio signal, via an audio reproduction system, in an operator environment, wherein the audio reproduction system provides the audio signal with a characteristic based upon a spatial relationship between a listener location and the simulated location in the virtual audio environment.

16. The system of claim 15, wherein the audio signal corresponds to verbal communication by a person in the patient environment.

17. The system of claim 15, wherein the audio signal corresponds to an audio output of a medical device in the patient environment.

18. The system of claim 15, wherein the tracking information is received from a tracking device attached to the source of the audio signal.

19. The system of claim 15, wherein determining the simulated location of the audio signal in the virtual audio environment includes altering the location of the source of the audio signal from the patient environment.

20. The system of claim 15, wherein determining the simulated location of the audio signal in the virtual audio environment includes matching the location of the source of the audio signal from the patient environment.

\* \* \* \* \*